United States Patent
Okamoto et al.

(10) Patent No.: US 9,012,657 B2
(45) Date of Patent: Apr. 21, 2015

(54) METHOD FOR PRODUCING PYRAZOLE COMPOUND

(75) Inventors: Masamune Okamoto, Fujimino (JP); Hideaki Imura, Iruma-gun (JP); Naoto Takada, Iruma-gun (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/009,483

(22) PCT Filed: Jun. 18, 2012

(86) PCT No.: PCT/JP2012/065459
§ 371 (c)(1),
(2), (4) Date: Oct. 2, 2013

(87) PCT Pub. No.: WO2012/176717
PCT Pub. Date: Dec. 27, 2012

(65) Prior Publication Data
US 2014/0107347 A1 Apr. 17, 2014

(30) Foreign Application Priority Data

Jun. 22, 2011 (JP) ................. 2011-138737
Jun. 22, 2011 (JP) ................. 2011-138740

(51) Int. Cl.
C07D 231/10 (2006.01)
C07D 231/28 (2006.01)
C07D 231/14 (2006.01)
(52) U.S. Cl.
CPC ............ *C07D 231/28* (2013.01); *C07D 231/14* (2013.01)
(58) Field of Classification Search
USPC ...................................... 548/374.1
See application file for complete search history.

(56) References Cited

U.S. PATENT DOCUMENTS

| | | | |
|---|---|---|---|
| 6,706,911 B1 | 3/2004 | Lui et al. | |
| 7,358,387 B2 | 4/2008 | Lantzsch et al. | |
| 7,652,004 B2 | 1/2010 | Martin et al. | |
| 7,728,029 B2 | 6/2010 | Anderson et al. | |
| 7,816,391 B2 | 10/2010 | Packer et al. | |
| 7,863,460 B2 | 1/2011 | Aihara et al. | |
| 8,344,016 B2 | 1/2013 | Packer et al. | |
| 2006/0252944 A1 | 11/2006 | Lantzsch et al. | |
| 2007/0225280 A1 | 9/2007 | Anderson et al. | |
| 2008/0154045 A1 | 6/2008 | Aihara et al. | |
| 2009/0074715 A1 | 3/2009 | Martin et al. | |
| 2009/0221663 A1 | 9/2009 | Packer et al. | |
| 2010/0022782 A1* | 1/2010 | Zierke et al. ............ 548/374.1 |
| 2011/0009642 A1 | 1/2011 | Pazenok | |
| 2011/0224273 A1 | 9/2011 | Packer et al. | |
| 2013/0197239 A1 | 8/2013 | Pazenok et al. | |

FOREIGN PATENT DOCUMENTS

| | | |
|---|---|---|
| CN | 1604889 A | 4/2005 |
| JP | 8-20560 A | 1/1996 |
| JP | 2000-128763 A | 5/2000 |
| JP | 2000-212166 A | 8/2000 |
| JP | 2005-511782 A | 4/2005 |
| JP | 2007-509850 A | 4/2007 |

(Continued)

OTHER PUBLICATIONS

Rai et al., "Synthesis, characterization and antibacterial activity of 2-[1-(5-chloro-2-methoxy-phenyl)-5-methyl-1*H*-pyrazol-4-yl]-5-(substituted-phenyl)-[1,3,4]oxadiazoles", European Journal of Medicinal Chemistry, 2009, pp. 4522-4527, vol. 44.

(Continued)

*Primary Examiner* — Samantha Shterengarts
(74) *Attorney, Agent, or Firm* — Crowell & Moring LLP

(57) ABSTRACT

A method for producing a pyrazole compound of the general formula (5) includes reacting a 2-acyl-3-aminoacrylic acid ester of the general formula (1) with a hydrazine of the general formula (4) in the presence of a base

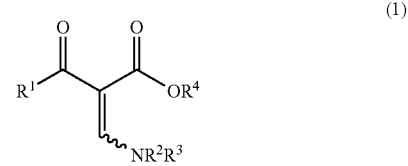
(1)

where $R^1$, $R^2$, $R^3$ and $R^4$ each independently represent an alkyl group

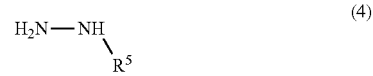
(4)

wherein $R^5$ represents an alkyl group or an aryl group

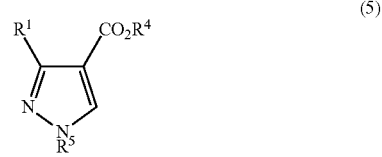
(5)

wherein $R^1$, $R^4$ and $R^5$ have the same meanings as above.

It is possible by this production method to produce the 1,3-disubstituted pyrazol-4-carboxylic acid ester at a high yield and selectivity and with less discoloration.

9 Claims, No Drawings

(56) References Cited

FOREIGN PATENT DOCUMENTS

| | | |
|---|---|---|
| JP | 2009-530343 A | 8/2009 |
| JP | 2010-518063 A | 5/2010 |
| JP | 2010-203107 A | 9/2010 |
| JP | 2012-56906 A | 3/2012 |
| WO | WO 03/051820 A1 | 6/2003 |
| WO | WO 2005/042468 A1 | 5/2005 |
| WO | WO 2006/090778 A1 | 8/2006 |
| WO | WO 2009/029384 A2 | 3/2009 |
| WO | WO 2009/106230 A2 | 9/2009 |

OTHER PUBLICATIONS

International Search Report with English translation dated Aug. 14, 2012 (five (5) pages).
Japanese-language Written Opinion (PCT/ISA/237) dated Aug. 14, 2012 (six (6) pages).
Chinese Office Action dated Sep. 4, 2014 (eight (8) pages).
Japanese Office Action dated Dec. 24, 2014 (Three (3) pages).

* cited by examiner

METHOD FOR PRODUCING PYRAZOLE COMPOUND

TECHNICAL FIELD

The present invention relates to a method for producing a pyrazole compound that is useful as an intermediate for pharmaceutical and agrichemical products.

BACKGROUND ART

There are known many methods for producing a 1,3-disubstituted pyrazole-4-carboxylic acid ester by reaction of a 2-alkoxymethyleneacylacetate, in which an alkoxy group acts as a leaving group, with a hydrazine (see e.g. Patent Documents 1 to 3). For instance, Patent Document 3 discloses that an isomer mixture of ethyl 3-(difluoromethyl)-1-methyl-1H-pyrazole-4-carboxylate and ethyl 5-(difluoromethyl)-1-methyl-1H-pyrazole-4 carboxylate can be obtained from an aqueous solution of ethyl 2-ethoxymethylene-4,4-difluoroacetoacetate and methylhydrazine.

On the other hand, there have been proposed methods for producing a 1,3-disubstituted pyrazole-4-carboxylic acid ester by reaction of a reaction substrate in which an amino group acts as a leaving group. For instance, Patent Document 4 discloses that a 3-perhalo-substituted pyrazole can be obtained by reaction of a 2-perhaloacyl-3-aminoacrylic acid derivative with a hydrazine. Patent Document 5 discloses that a 89.2:10.8 mixture of ethyl 3-(difluoromethyl)-1-methyl-1H-pyrazole-4-carboxylate and its isomer (ethyl 5-(difluoromethyl)-1-methyl-1H-pyrazole-4-carboxylate) can be obtained by reaction of ethyl 2-(difluoroacetyl)-3-(dimethylamino)acrylate with methylhydrazine.

PRIOR ART DOCUMENTS

Patent Documents

Patent Document 1: Japanese Laid-Open Patent Publication No. 2000-128763
Patent Document 2: Japanese Laid-Open Patent Publication No. 2000-212166
Patent Document 3: International Application Publication No. 06/090778
Patent Document 4: Published Japanese Translation of International Application Publication No. 2005-511782
Patent Document 5: Published Japanese Translation of International Application Publication No. 2007-509850

SUMMARY OF THE INVENTION

Problems to be Solved by the Invention

In the case of producing ethyl 3-(difluoromethyl)-1-methyl-1H-pyrazole-4-carboxylate according to the method of Patent Document 5, the resulting product has discoloration. Although the cause of such discoloration is not clear, the presence of any unidentified substance is suspected due to the fact that both of 3-(difluoromethyl)-1-methyl-1H-pyrazole-4-carboxylate and its isomer, i.e., ethyl 5-(difluoromethyl)-1-methyl-1H-pyrazole-4-carboxylate are solid and colorless. For use of the pyrazole compound as an intermediate for pharmaceutical and agrichemical products, it is not desired that the unidentified substance is contained even in a small amount in the pyrazole compound.

It is accordingly an object of the present invention to produce a 1,3-disubstituted pyrazole-4-carboxylic acid ester with less discoloration.

Means for Solving the Problems

The present inventors have found that, in the case of producing 3-(difluoromethyl)-1-methyl-1H-pyrazole-4-carboxylate according to the method of Patent Document 5, it is possible to remarkably reduce the occurrence of discoloration in the resulting product by adding ethyl 2-(difluoroacetyl)-3-(dimethylamino)acrylate to methylhydrazine in toluene etc. in the presence of a base. The present invention is based on this finding. Despite the fact that an ester such as ethyl 2-(difluoroacetyl)-3-(dimethylamino)acrylate is readily hydrolyzed upon contact with an aqueous basic solution, there occurs no hydrolysis under the reaction conditions of the present invention so that the 3-(difluoromethyl)-1-methyl-1H-pyrazole-4-carboxylate can be obtained at a high yield.

It is herein conceivable to produce ethyl 2-(difluoroacetyl)-3-(dimethylamino)acrylate by using a dialkylaminoacrylic acid ester as a starting material. In this case, the production of ethyl 3-(difluoromethyl)-1-methyl-1H-pyrazole-4-carboxylate proceeds in the following first and second steps: acylation and cyclization.

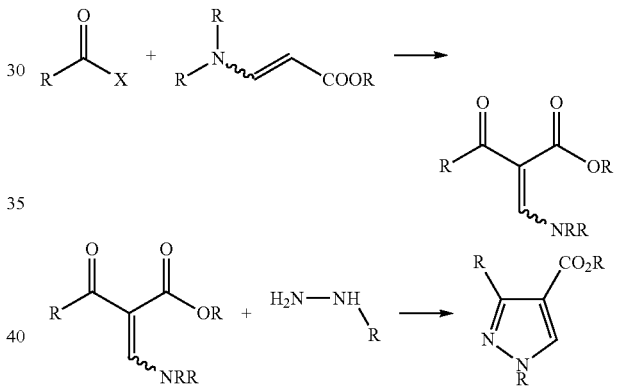

In the acylation of the first step (acylation step), an organic base such as triethylamine is often added in order to prevent generation of a trimesic acid ester. As hydrogen halide is by-produced as an acid component in the acylation, the organic base such as triethylamine is combined with such a by-produced acid to form a salt of the organic base and hydrogen halide (hereinafter sometimes simply referred to as "salt").

The present inventors have made research about the influence of the salt on the cyclization and found that: the presence of the salt leads to an increase in the generation of the isomer (1,5-disubstituted pyrazole-4-carboxylic acid ester): and the ratio of the isomer can be reduced by purification e.g. water washing and drying of the reaction solution obtained by the acylation step. However, the yield of the acylation reaction product becomes lowered due to such purification process. This results in a deterioration of the target product yield. The present inventors have found, as a result of further research, that it is possible to obtain the 1,3-disubstituted pyrazole-4-carboxylic acid ester at a high yield, with less isomer, by performing the cyclization of the second step (cyclization step) upon the addition of an inorganic base such as potassium hydroxide to the reaction solution obtained by the acylation step without removing the salt from the reaction solution.

Namely, the present invention includes the following aspects.

[Inventive Aspect 1]

A method for producing a pyrazole compound of the general formula (5), comprising: a reaction step of reacting a 2-acyl-3-aminoacrylic acid ester of the general formula (1) with a hydrazine of the general formula (4) in the presence of a base

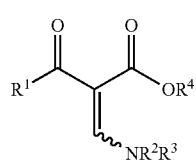
(1)

where $R^1$, $R^2$, $R^3$ and $R^4$ each independently represent an alkyl group;

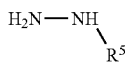
(4)

wherein $R^5$ represents an alkyl group or an aryl group;

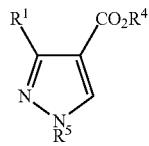
(5)

wherein $R^1$, $R^4$ and $R^5$ have the same meanings as above.

[Inventive Aspect 2]

The method for producing the pyrazole compound according to Inventive Aspect 1, wherein the base is an inorganic base.

[Inventive Aspect 3]

The method for producing the pyrazole compound according to Inventive Aspect 2, wherein the base is an alkali metal hydroxide.

[Inventive Aspect 4]

The method for producing the pyrazole compound according to any one of Inventive Aspects 1 to 3, wherein $R^1$ is a halogenated alkyl group of 1 to 10 carbon atoms.

[Inventive Aspect 5]

The method for producing the pyrazole compound according to Inventive Aspect 4, wherein $R^1$ is a fluoroalkyl group of 1 to 4 carbon atoms.

[Inventive Aspect 6]

The method for producing the pyrazole compound according to Inventive Aspect 5, wherein $R^1$ is a trifluoromethyl group or a difluoromethyl group.

[Inventive Aspect 7]

The method for producing the pyrazole compound according to Inventive Aspect 4, wherein $R^1$ is a chloroalkyl group of 1 to 4 carbon atoms.

[Inventive Aspect 8]

The method for producing the pyrazole compound according to Inventive Aspect 7, wherein $R^1$ is a dichloromethyl group.

[Inventive Aspect 9]

The method for producing the pyrazole compound according to any one of Inventive Aspects 1 to 8, wherein the reaction step includes the following two steps (substeps):

a first step of obtaining a reactor content containing the 2-acyl-3-aminoacrylic acid ester of the general formula (1) by reacting a carboxylic acid halide of the general formula (2) with a dialkylaminoacrylic acid ester of the general formula (3) in the presence of an organic base

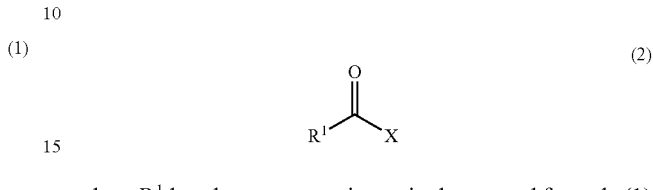
(2)

where $R^1$ has the same meaning as in the general formula (1)

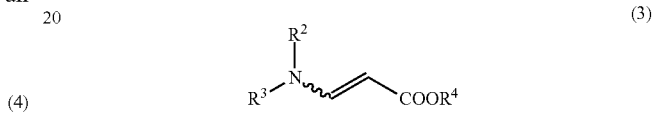
(3)

where $R^2$, $R^3$ and $R^4$ have the same meanings as in the general formula (1); and a second step of forming the pyrazole compound of the general formula (5) by mixing the reactor content obtained by the first step, an inorganic base as the base and a substituted hydrazine as the hydrazine of the general formula (4).

[Inventive Aspect 10]

The method for producing the pyrazole compound according to Inventive Aspect 9, wherein, in the second step, the pyrazole compound of the general formula (5) is formed by mixing a composition containing the reactor content obtained by the first step and the base with a composition containing the substituted hydrazine.

[Inventive Aspect 11]

The method for producing the pyrazole compound according to Inventive Aspect 9 or 10, wherein the organic base used in the first step is a tertiary amine; and wherein the inorganic base used in the second step is either potassium hydroxide or sodium hydroxide.

[Inventive Aspect 12]

The method for producing the pyrazole compound according to any one of Inventive Aspects 9 to 11, wherein the carboxylic acid halide of the general formula (2) is difluoroacetic acid fluoride.

It is possible in the present invention to produce the 1,3-disubstituted pyrazole-4-carboxylic acid ester at a high yield and selectivity and with less discoloration. Further, the content of an isomer (1,5-disubstituted pyrazole-4-carboxylic acid ester) in the product can be limited to a very low level in the present invention. In particular, in a preferred embodiment of the present invention, the 1,3-disubstituted pyrazole-4-carboxylic acid ester can be produced efficiently with less isomer by acylation of a dialkylaminoacrylic acid ester as a starting material in the presence of an organic base, and then, cyclization of the acylation reaction product upon the addition of an inorganic base to the reactor content without removing a salt from the reactor content.

DETAILED DESCRIPTION OF THE EMBODIMENTS

Hereinafter, the present invention will be described below in detail.

In the following description, a 1,3-disubstituted pyrazole-4-carboxylic acid ester and a 1,5-disubstituted pyrazole-4-carboxylic acid ester may be abbreviated as "1,3-isomer" and "1,5-isomer", respectively, for the purpose of distinguishing a pyrazole compound with 1,3-substituents from a pyrazole compound with 1,5-substitutents. These abbreviations are not however intended to mean specific pyrazole compounds. Furthermore, the term "alkyl group" refers to either a straight, branched or cyclic alkyl group; and the terms "alkyl group" and "aryl group" refer to alkyl and aryl groups with or without substituents, respectively.

<Synthesis of 2-acyl-3-aminoacrylic acid ester (Acylation)>

A 2-acyl-3-aminoacrylic acid ester of the general formula (1) is synthesized by reaction (acylation) of a carboxylic acid halide of the general formula (2) and a dialkylaminoacrylic acid ester of the general formula (3).

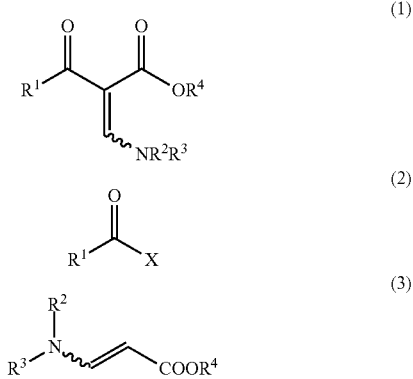

In the general formulas (1) to (3), $R^1$, $R^2$, $R^3$ and $R^4$ each independently represents an alkyl group. The alkyl group is preferably of 1 to 10 carbon atoms, more preferably 1 to 4 carbon atoms. Further, the alkyl group may have any hydrogen atom or atoms substituted by a halogen atom. As the halogen atom, there can be used fluorine, chlorine, bromine or iodine. Among others, fluorine or chlorine is preferred as the halogen atom. Examples of the alkyl group are methyl, ethyl, n-propyl, isopropyl, n-butyl, s-butyl, t-butyl, cyclohexyl, cyclopentyl and those obtained by substation of any of hydrogen atoms of these alkyl groups by a halogen atom.

Preferably, $R^1$ is a halogenated alkyl group of 1 to 4 carbon atoms, more preferably a fluoroalkyl, chloroalkyl or chlorofluoroalkyl group of 1 to 4 carbon atoms. Specific examples of the halogenated alkyl group are trifluoromethyl, difluoromethyl, monofluoromethyl, pentafluoroethyl, 2,2,2-trifluoroethyl, 2,2-difluoroethyl, 1,1,2,2-tetrafluoroethyl, trichloromethyl, dichloromethyl, monochloromethyl, pentachloroethyl, 2,2,2-trichloroethyl, 2,2-dichloroethyl, 1,1,2,2-tetrachloroethyl, chlorodifluoromethyl and dichlorofluoromethyl. Among others, trifluoromethyl, difluoromethyl or dichloromethyl is particularly preferred.

There is no particular limitation on $R^2$ and $R^3$ because $R^2$ and $R^3$ act as a leaving group $NR^2R^3$. Each of $R^2$ and $R^3$ may not be halogen-substituted. Among the above alkyl groups, methyl or ethyl is preferred as $R^2$, $R^3$. It is particularly preferred that both of $R^2$ and $R^3$ are methyl.

$R^4$ is determined depending on the purpose of reaction using the pyrazole compound as a reaction substrate. In the case where the pyrazole compound is converted to a carboxylic acid by deprotection of $R^4$, $R^4$ acts as a leaving group. In this case, there is no particular limitation on $R^4$. Among the above alkyl groups, ethyl or isopropyl is preferred as $R^4$.

In the general formula (2), X represents a halogen atom such as fluorine, chlorine, bromine or iodine.

The carboxylic acid halide can be prepared by any known method. For example, it is feasible to prepare a carboxylic acid chloride by chlorinating a corresponding carboxylic acid with a chlorinating agent such as thionyl chloride or by oxidizing a halogenated hydrocarbon. It is also feasible to prepare a carboxylic acid fluoride by thermal decomposition of 1-alkoxy-1,1,2,2-tetrafluoroethane in the presence of a catalyst (see e.g. Japanese Laid-Open Patent Publication No. 8-20560).

The acylation is generally performed in a nonaqueous solvent. As the nonaqueous solvent, there can be used an aliphatic or aromatic hydrocarbon. Examples of the nonaqueous hydrocarbon solvent are petroleum ether, n-hexane, n-heptane, cyclohexane, benzene, toluene, xylene, decalin and halogenated hydrocarbons such as chlorobenzene, dichlorobenzene, dichloromethane, chloroform, tetrachloromethane, dichloroethane and trichloroethane. Among others, toluene, xylene, chlorobenzene, n-hexane or cyclohexane is preferred. Particularly preferred is toluene or xylene. The above solvents can be used solely or in the form of a mixture thereof.

Further, the acylation is generally performed in the presence of a base. The addition of the base makes it possible to capture a hydrogen halide such as HF or HCl generated in the acylation and thereby prevent generation of a trimesic acid ester as a by-product. As the base, there can be used a tertiary amine, a pyridine or a pyridine derivative (hereinafter sometimes just referred to as "pyridine") or the like. Examples of the pyridine or pyridine derivative are pyridine, 2-, 3- or 4-methylpyridine, 2-methyl-5-ethyl-pyridine, 4-ethyl-2-methylpyridine, 3-ethyl-4-methylpyridine, 2,4,6-collidine, 2- or 4-n-propylpyridine, 2,6-dimethylpyridine (lutidine), 4-dimethylaminopyridine, quinoline and quinaldine. Among others, pyridine, 2-methyl-5-ethylpyridine, 2,4,6-collidine, quinoline or quinaldine is preferred. Particularly preferred is pyridine. Examples of the tertiary amine are: symmetric tertiary amines such as trimethylamine, triethylamine, tri-n-propylamine, tri-isopropylamine, tri-n-butylamine, tri-isobutylamine, tri-sec-butylamine, tri-tert-butylamine, tri-n-amylamine, tri-isoamylamine, tri-sec-amylamine and tri-tert-amylamine; and asymmetric tertiary amines such as N-methyldi-n-butylamine, N-methyldiisobutylamine, N-methyldi-tert-butylamine, N,N-diisopropylbutylamine, N,N-dimethyldecylamine, N,N-dimethylundecylamine, N,N-dimethyldodecylamine and N-methyldihexylamine. It is preferable to use a symmetric amine in terms of boiling point, water solubility and availability. Among others, trimethylamine, triethylamine, tri-n-propylamine, tri-isopropylamine or tri-n-butylamine is preferred. More preferred is triethylamine. In the present production method, pyridine or triethylamine is particularly preferred as the base.

The acylation is preformed at a temperature of −20° C. to +50° C., preferably −10° C. to +45° C., more preferably 0 to 40° C. As the reaction is not influenced by the reaction pressure, there is no particular limitation on the reaction pressure. In general, it suffices to perform the acylation under pressure conditions from atmospheric pressure to about 1 MPa although the acylation can be performed under pressurized conditions of about 0.1 to 10 MPa. The reaction time varies depending on the reaction temperature and the content ratio of the reagent. The reaction time is generally about 10 minutes to 10 hours. The reaction time can be determined on the basis of reduction or disappearance of the reaction substrate as a guideline by monitoring the progress of the reaction.

In the acylation, the dialkylaminoacrylic acid ester is used in an amount of 0.5 to 3 mol, preferably 0.5 to 1.5 mol, more preferably 0.9 to 1.1 mol, per 1 mol of the carboxylic acid halide. The base is used in an amount of 0.5 to 5 mol, preferably 0.8 to 2 mol, more preferably 0.9 to 1.5 mol, per 1 mol of the carboxylic acid halide although it suffices to use the base in an equimolar amount to the carboxylic acid halide.

It is feasible to perform the acylation by dissolving the dialkylaminoacrylic acid ester and the base in the solvent, maintaining the resulting solution at a temperature lower than or equal to the upper limit of the reaction temperature and blowing the carboxylic acid halide into the solution. Alternatively, it is feasible to perform the acylation in a scrubber system. The base can be added continuously or successively with the progress of the reaction.

The thus-obtained reactor content (reaction solution), which contains the 2-acyl-3-aminoacrylic acid ester, can be used in the subsequent cyclization step without purification or after distillation of the residual solvent or base (e.g. removal of the solvent by flash distillation). In the case of using the organic base such as pyridine or trialkylamine for the purpose of preventing generation of the trimesic acid ester, the organic base forms a salt with the hydrogen halide generated in the acylation. The reactor content containing such a salt may directly be subjected to the subsequent cyclization step. However, there is a possibility that the by-production of an unfavorable isomer (1,5-disubstituted pyrazole-4-carboxylic acid ester) will be accelerated in the presence of the salt. It is desirable to remove the salt by washing with water etc. The recovery rate of the 2-acyl-3-aminoacrylic acid ester may however be lowered due to such water washing operation because of the high water solubility of the 2-acyl-3-aminoacrylic acid ester.

<Synthesis of Pyrazole Compound (Cyclization)>

The above-obtained 2-acyl-3-aminoacrylic acid ester of the general formula (1) is reacted with a hydrazine of the general formula (4) in the presence of a base, thereby synthesizing a pyrazole compound of the general formula (5).

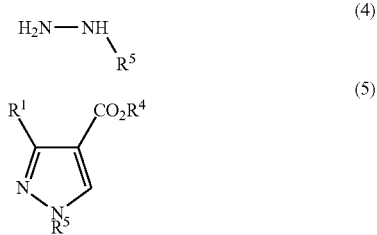

As the meanings of $R^1$, $R^2$, $R^3$ and $R^4$ in the general formulas (1) and (5) are the same as above, repeated explanations of $R^1$, $R^2$, $R^3$ and $R^4$ will be omitted herefrom.

In the general formulas (4) and (5), $R^5$ represents an alkyl or aryl group that may have a substituent. Preferably, $R^5$ is a straight, branched or cylic alkyl or alkoxyalkyl group of 1 to 10 carbon atoms or an aryl group. Any number of hydrogen atoms of the alkyl or alkoxy group may be substituted by a halogen atom. An oxygen atom of the alkoxy group may be replaced by a sulfur atom. As the halogen atom, there can be used fluorine, chlorine or bromine. Specific examples of the alkyl or aryl group as $R^5$ are methyl, ethyl, n-propyl, isopropyl, tert-butyl, difluoromethyl, trifluoromethyl, hydroxymethyl, hydroxyethyl, cyclopropyl, cyclopentyl, cyclohexyl and phenyl. Among others, methyl, ethyl, isopropyl, n-propyl or tert-butyl is preferred. Particularly preferred is methyl.

Preferred examples of the hydrazine of the general formula (4) are substituted hydrazines such as methylhydrazine and ethylhydrazine. It is preferable to use the hydrazine in solution form in terms of availability and ease of handling although the hydrazine can be used in anhydrous form.

The cyclization is preformed in the presence of the base. As the base, a water-soluble inorganic base is suitably used. The inorganic base is preferably a hydroxide, carbonate or hydrogencarbonate of alkaline-earth metal or alkali metal. It is particularly preferable to use a hydroxide of alkali metal as the base. Specific examples of the base are sodium hydroxide, potassium hydroxide, lithium hydroxide, sodium carbonate, potassium carbonate, potassium hydrogencarbonate and sodium hydrogencarbonate. Among others, sodium hydroxide, potassium hydroxide or lithium hydroxide is preferred. Sodium hydroxide or potassium hydroxide is more preferred. Particularly preferred is potassium hydroxide because of the high solubility in aqueous solvents and ease of operation such as purification. The base used is not necessarily of high-purity grade. It is economically favorable to use the base of general-purpose grade available as an ordinary industrial chemical or reagent.

In the cyclization, the base is generally used in an amount of 0.05 to 2 mol, preferably 0.2 to 0.6 mol, more preferably 0.3 to 0.5 mol, per 1 mol of the 2-acyl-3-aminoacrylic acid ester. If the amount of the base used is less than 0.05 mol, the decolorization effect may be low. If the amount of base used exceeds 2 mol, the yield of the target product may be lowered due to hydrolysis of the raw material or the reaction product.

It is a preferred embodiment of the present invention is to perform the acylation by the use of the organic base, and then, perform the cyclization by the addition of the inorganic base to the resulting reactor content without removing the salt from the reactor content. In general, the amount of generation of the isomer (1,5-disubstituted pyrazole-4-carboxylic acid ester) is increased in the presence of the salt in the cyclization reaction system. In the preferred embodiment of the present invention, however, it is possible to limit the amount of generation of the isomer (1,5-disubstituted pyrazole-4-carboxylic acid ester) to a low level when the cyclization is performed by the addition of the inorganic base without removing the salt from the reactor system. In this preferred embodiment, it is preferable to use a tertiary amine as the organic base in the acylation and to use potassium hydroxide or sodium hydroxide as the inorganic base in the cyclization. Further, it is feasible in the cyclization to the inorganic base in an amount of 1.1 to 1.3 mol, preferably 1.2 to 2 mol, more preferably 1.3 to 1.5 mol, per 1 mol of the 2-acyl-3-aminoacrylic acid ester in this preferred embodiment. If the amount of the inorganic base used is less than 1.1 mol, the 1,5-isomer retardation effect may be low. If the amount of the inorganic base used exceeds 3 mol, the yield of the target product may be lowered due to hydrolysis of the raw material or the reaction product. It is also preferable to use difluoroacetic acid fluoride as the carboxylic acid halide of the general formula (2).

The cyclization is preferably performed in the presence of a solvent. Examples of the solvent are: water; aliphatic, alicyclic or aromatic hydrocarbons such as petroleum ether, n-hexane, n-heptane, cyclohexane, benzene, toluene, xylene and decalin; halogenated hydrocarbons such as chlorobenzene, dichlorobenzene, dichloromethane, chloroform, tetrachloromethane, dichloroethane and trichloroethane; ethers such as diethyl ether, diisopropyl ether, methyl tert-butyl ether, methyl tert-amyl ether, dioxane, tetrahydrofuran, 1,2-dimethoxyethane, 1,2-diethoxyethane and anisole; alcohols such as methanol, ethanol, n-propanol, isopropanol, n-butanol, i-butanol, s-butanol, t-butanol and cyclohexanol; ketones such as acetone, methyl ethyl ketone, methyl isobutyl ketone and cyclohexanone; nitriles such as acetonitrile, propionitrile, n- or isobutyronitrile and benzonitrile; amides such as N,N-dimethylformamide, N,N-dimethylacetoamide, N,N-methylformanilide, N-methylpyrrolidone and hexamethylphosphoramide; sulfoxides such as dimethyl sulfoxide; and sulfolanes such as sulfolane. Among others, a hydrocarbon or halogenated hydrocarbon solvent is preferred. More preferred is an aromatic hydrocarbon solvent. More specifically, toluene, xylene, chlorobenzene, n-hexane or cyclohexane is preferred as the aromatic hydrocarbon solvent. Particularly preferred is toluene or xylene. Further, it is preferable in this pyrazole synthesis step to use the same solvent as that used in the preceding 2-acyl-3-aminoacrylic acid ester synthesis step. It is particularly preferable to use the same solvent in the 2-acyl-3-aminoacrylic acid ester synthesis and pyrazole synthesis steps in the case where the reaction product of the preceding 2-acyl-3-aminoacrylic acid ester synthesis step is subjected to pyrazole cyclization reaction without separation or purification. The above solvents can be used in the form of a mixture of two or more thereof.

It is preferable to perform the cyclization under low-temperature conditions. In view of practicality, the cyclization is performed at $-78°$ C. to $+30°$ C., preferably $-30°$ C. to $+20°$ C. The selectivity of the cyclization reaction is high under low-temperature conditions. It is however unfavorable to set the cyclization temperature to be lower than $-78°$ C. in terms of operation difficulty due to solidification or viscosity increase of the solvent, increase in cooling cost, decrease in reaction rate etc. It is also unfavorable to set the cyclization temperature to be higher than $+30°$ C. in terms of decrease in selectivity due to occurrence of a side reaction. As the reaction is not influenced by the reaction pressure within a normal pressure range, there is no particular limitation on the reaction pressure. The cyclization can be preformed under pressurized conditions or reduced pressure conditions. In general, it suffices to perform the cyclization under atmospheric pressure conditions without conscious pressurization or pressure reduction. For safety, it is not preferable to bring the hydrazine, which is a strong reducing agent, into contact with air. The cyclization is thus preferably preformed in the atmosphere of nitrogen, argon etc. The reaction time varies depending on the reaction temperature and the like. The reaction time is generally about 10 minutes to 10 hours.

In the cyclization reaction, there is no particular limitation on the order of introduction of the reaction substrates and subsidiary materials into the reaction system. It is easy to handle the base in the form of a composition containing the base, the hydrazine and the solvent and is thus preferable to bring this composition into contact with a composition to containing the 2-acyl-3-aminoacrylic acid ester. As a matter of course, the object of the present invention can be achieved by any technique according to such an intention. More specifically, one of the above compositions can preferably be introduced to the other composition by dropping or injection with the use of a metering pump etc. In the above preferred embodiment, the reactor content obtained by the acylation step can be mixed with the inorganic base and the substituted hydrazine. It is preferable to mix a composition containing the reactor content obtained by the acylation step and the inorganic base with a composition containing the substituted hydrazine. The mixing is preferably gradually carried out in such a manner that the reaction temperature does not exceeds the upper limit of the above temperature range by monitoring the progress of the reaction such as temperature increase and component change of the reactor content. It is further preferable to stir the reactor content.

The pyrazole compound can be purified by an ordinary purification process.

One example of purification process includes washing the reactor content with water and distilling the resulting organic phase to remove the solvent from the organic phase. The components of the reactor content vary depending on the purification process between the acylation step and the cyclization step, the use of the solvent in the acylation step and the cyclization step etc. By the two-phase separation of the reactor content, the pyrazole compound is extracted into the organic phase. In this organic phase, the organic base and the organic solvent (when used) used in the acylation step may also be contained. On the other hand, an eliminated secondary amine such as dimethylamine is extracted into the aqueous phase. The inorganic fluoride such as potassium fluoride, an inorganic hydroxide and the hydrazine may also be contained in the aqueous phase. It is feasible to recover the pyrazole compound by flash distillation of the organic phase. In this case, the distilled solvent containing the base can be reused in the acylation step. It is alternatively feasible to recover the pyrazole compound by washing the organic phase with water to remove therefrom the organic base, and then, distilling the solvent out from the organic solvent. The thus-purified pyrazole compound may further be subjected to drying by heating or under a reduced pressure.

It is feasible to remove the isomer (1,5-disubstituted pyrazole-4-carboxylic acid ester) contained in the 1,3-disubstituted pyrazole-4-carboxylic acid ester by crystallization using a solvent. Alternatively, it is feasible to convert the 1,3-disubstituted pyrazole-4-carboxylic acid ester and its isomer to a 1,3-disubstituted pyrazole-4-carboxylic acid by hydrolysis, and then, obtain the 1,3-disubstituted pyrazole-4-carboxylic acid ester by recrystallization. The 1,3-disubstituted pyrazole-4-carboxylic acid ester may further be purified with the use of an adsorption column etc.

It is effective to wash, with a nonpolar solvent, the 1,3-disubstituted pyrazole-4-carboxylic acid ester produced in the present production method. The 1,3-disubstituted pyrazole-4-carboxylic acid ester can be purified to a high purity level of 99.9% or higher by washing with the nonpolar solvent in place of recrystallization treatment. There is no particular limitation on the nonpolar solvent. Examples of the nonpolar solvent are hydrocarbons such as cyclohexane, pentane, hexane and heptane. The washing is preferably performed at a temperature of 0 to $25°$ C. If the washing temperature is lower than $0°$ C., the impurity removal efficiency may be low. If the washing temperature is higher than $25°$ C., the 1,3-disubstituted pyrazole-4-carboxylic acid ester may be eluted and lowered in recovery rate. There can be adopted any washing technique such as washing by stirring, washing by pouring or combination thereof. It is preferable to first perform washing by stirring, filtration, and then, washing by pouring.

Moreover, it is feasible to remove the polar substance or specific impurity by dissolving, in an organic solvent, the 1,3-disubstituted pyrazole-4-carboxylic acid ester containing the 1,5-isomer, and then, bringing the resulting treatment solution into contact with hydrochloric acid. In this case, the organic solvent is preferably of low water solubility. Examples of such an organic solvent are benzene, toluene, xylene, ethylbenzene, diisopropyl ether, methylene chloride and chloroform. Among others, toluene or xylene is preferred. The treatment solution can be prepared by mixing the pyrazole compound with the above solvent. In the case where the organic solvent is contained in the reactor content after the cyclization step, the reactor content may directly be subjected to washing with water to remove therefrom the secondary amine etc. The contact temperature is generally 0 to 80° C. It suffices to set the contact temperature to an ordinary temperature without heating or cooling. Although there is no particular limitation on the capacity ratio of the treatment solution and the hydrochloric acid, the capacity ratio of the treatment solution and the hydrochloric acid is preferably in the range of 9/1 to 1/1. If the amount of the hydrochloric acid used exceeds the above range, the space yield of the contact treatment may be deteriorated. If the amount of the hydrochloric acid used is less than the above range, there may occur an unfavorable result such as increase of treatment time or insufficiency of treatment efficiency. The treatment time varies depending on the content of the polar substance etc., the concentration of the hydrochloric acid, the capacity ratio of the treatment solution and the hydrochloric acid, the state of mixing of the treatment solution etc. In general, the treatment time is in a range of 30 minutes to 3 hours. The contact treatment can be performed by any means such as an ordinary stirring tank, a static mixer or a pump circulation system. It is easy to perform the contact treatment by mixing the treatment solution with the hydrochloric acid in a stirring tank, leaving the resulting solution still and thereby separating the polar substance or specific impurity. The pyrazole compound can be recovered by, after the contact treatment, separating the organic treatment solution from the hydrochloric acid and distilling the solvent from the organic treatment solution.

EXAMPLES

The present invention will be described in more detail below by way of the following examples. It should be noted that the following examples are illustrative and are not intended to limit the present invention thereto. The analysis of organic substances in each reaction solution was contacted by a gas chromatograph (with a FID detector). The composition analysis results are in units of area %. The content of ethyl 2-(difluoroacetyl)-3-(dimethylamino)acrylate (DFAAE) in the reaction solution was determined based on the mass of a solid substance obtained by distilling toluene from the reaction solution after washing the reaction solution with water.

Comparative Example 1

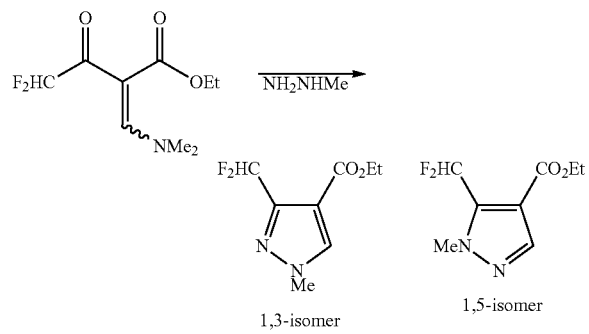

A 500-ml three-neck flask was equipped with a dropping funnel and a thermometer and sealed under a nitrogen balloon. Into this flask, 9.0 g of water, 100 ml of toluene and 6.0 g (0.13 mol) of monomethylhydrazine were placed. The resulting solution was cooled, with stirring, to −10° C. or lower in a low-temperature thermostat whose temperature was set to −15° C. Then, 110 g of a toluene solution containing 22.6 mass % of ethyl 2-(difluoroacetyl)-3-(dimethylamino)acrylate (DFAAE) was dropped into the flask through the dropping funnel by controlling the dropping rate of the toluene solution in such a manner that the inside temperature of the flask did not exceed −10° C. After completion of the dropping, the reaction was continued for 1 hour at −12° C. The inside temperature of the flask was then raised to 0° C. The thus-obtained reaction solution was separated with the addition of 100 ml of water. The organic phase was recovered by a separatory funnel and washed with 100 ml of water, thereby yielding a toluene solution (193 g).

The above-yielded toluene solution was analyzed by a gas chromatograph. As a result, it was confirmed that: the content of ethyl 3-(difluoromethyl)-1-methyl-1H-pyrazole-4-carboxylate (target compound, 1,3-isomer) was 9.7 area %; the content of ethyl 5-(difluoromethyl)-1-methyl-1H-pyrazole-4-carboxylate (1,5-isomer) was 0.7 area %; and the content of other compounds, except toluene, was 0.03 area %. The ratio of the target compound and the isomer was 93.7:6.7. Next, 100 ml of the toluene solution was taken as a sample into a colorimeter and visually compared with standard Hazen solutions. The number of the standard Hazen solution closest in color to the sample was 500. Further, the toluene solution was also compared with JIS color samples. The color of the toluene solution was closest to strongly reddish "Himawari-iro" among the JIS color samples.

Example 1

The same experiment as that of Comparative Example 1 was carried out, except that an aqueous solution of NaOH (1.8 g) in 9.0 g of water was used in place of 9.0 g of water, thereby yielding a toluene solution (191 g).

The above-yielded toluene solution was analyzed by a gas chromatograph. As a result, it was confirmed that: the content of target compound was 9.58 area %; the content of 1,5-isomer: 0.02 area %; and the content of other compounds, except toluene, was 0.01 area %. Next, 100 ml of the toluene solution was taken as a sample into a colorimeter and visually compared with standard Hazen solutions. The number of the standard Hazen solution closest in color to the sample was 300. Further, the toluene solution was also compared with JIS color samples. The color of the toluene solution was closest to "Kariyasu-iro", which was less reddish than that of Comparative Example 1.

Furthermore, the toluene solution was concentrated by a rotary evaporator, admixed with 25 g of hexane and stirred at 5° C. for 1 hour by a magnetic stirrer. The resulting precipitate was filtrated out, washed with hexane and dried under vacuum, thereby obtaining 17.7 g of a white crystal. This crystal was dissolved in acetone and analyzed by a gas chromatograph. It was confirmed that the content of ethyl 3-(difluoromethyl)-1-methyl-1H-pyrazole-4-carboxylate in the crystal was 99.9 area %.

Preparation Example

Preparation of Standard Hazen Solutions

The standard Hazen solutions used in Comparative Example 1 and Example 1 as indicated in TABLE 1 were prepared by diluting, with distilled water, a color standard solution (1000 degree) manufactured by Kanto Chemical Co., Ltd. For example, the standard Hazen solution No. 300 was prepared by placing 30 ml of the raw color standard solution into a measuring flask and diluting the solution to 100 ml with distilled water. The same applies to the others.

The test results of Comparative Example 1 and Example 1 are indicated in TABLE 1.

TABLE 1

| | Isomer ratio | | Number of standard Hazen solution | Closest color among JIS color samples | | |
|---|---|---|---|---|---|---|
| | 1,3-isomer | 1,5-isomer | | JIS color name | Hexadecimal color code | RGB value |
| Comparative Example 1 | 93.3 | 6.7 | 500 | Himawari-iro | #FFBB00 | 2551870 |
| Example 1 | 99.8 | 0.2 | 300 | Kariyasu-iro | #EAD56B | 234213103 |

1,3-isomer: ethyl 3-(difluoromethyl)-1-methyl-1H-pyrazole-4-carboxylate
1,5-isomer: ethyl 5-(difluoromethyl)-1-methyl-1H-pyrazole-4-carboxylate As is seen from TABLE 1, the 1,3-disubstituted pyrazole-4-carboxylic acid ester was produced efficiently with less discoloration by reaction of the 2-acyl-3-amonoacrylic acid ester with the hydrazine in the presence of the base.

Synthesis Example 1

Synthesis of ethyl 2-(difluoroacetyl)-3-(dimethylamino)acrylate (DFAAE)

A 2000-ml three-neck flask was equipped with a blowing tube, a thermometer and a dry-ice condenser and sealed with nitrogen. Into this flask, 143 g of ethyl 3-N,N-dimethylaminoacrylate (DMAE), 570 g of toluene and 111 g of triethylamine ($Et_3N$) were placed. The resulting solution was stirred while cooling the flask at 20° C. in a water bath. Then, 111 g of difluoroacetic acid fluoride (purity: 95%) was introduced at a rate of 1 g/min into the flask reactor through the blowing tube After completion of the introduction, the reaction was continued for 1 hour by stirring the reaction solution at 30° C. and completed.

The amount of the reactor content (reaction solution) thus obtained was 927 g. The reaction solution was analyzed by a gas chromatograph. As a result, it was confirmed that: the content of DFAAE was 8.22 area %; the total content of $Et_3N$ and a salt of $Et_3N$ and hydrogen fluoride ($Et_3N$.nHF salt) was 10.48 area % (the $Et_3N$.nHF salt showed a broad peak of about 1 area %); the content of DMAE was 0.082 area %; and the content of toluene was 80.62 area %.

Comparative Example 2

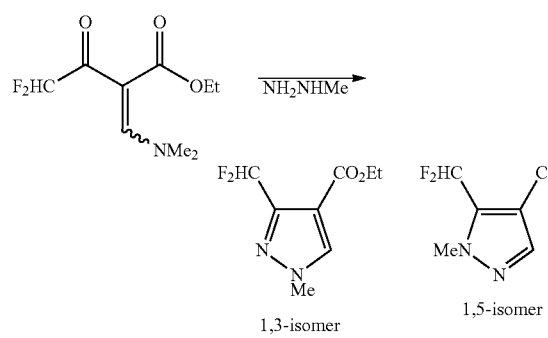

A 500-ml three-neck flask was equipped with a dropping funnel and a thermometer and sealed under a nitrogen balloon. Into this flask, 9.0 g of water, 100 ml of toluene and 6.0 g (0.13 mol) of monomethylhydrazine were placed. The resulting solution was cooled, with stirring, to −10° C. or lower in a low-temperature thermostat whose temperature was set to −15° C. Then, 102 g of the solution (reaction solution, DFAAE: 0.11 mol) obtained in Synthesis Example 1 was gradually dropped into the flask through the dropping funnel in such a manner that the inside temperature of the flask did not exceed −10° C. After completion of the dropping, the reaction solution was kept stirred for 1 hour at −12° C. The inside temperature of the flask was then raised to 0° C. The reaction solution was then separated with the addition of 100 ml of water. The organic phase was recovered by a separatory funnel, washed with 100 ml of water, dried with magnesium sulfate, and then, subjected to filtration and solvent distillation. As a result, 21.0 g of a crude pyrazole was yielded (crude product yield: 93.6%). The crude pyrazole was dissolved in acetone. The thus-obtained acetone solution was analyzed by a gas chromatograph. As a result, it was confirmed that the total pyrazole purity (i.e., the total purity of ethyl 3-(difluoromethyl)-1-methyl-1H-pyrazole-4-carboxylate and ethyl 5-(difluoromethyl)-1-methyl-1H-pyrazole-4-carboxylate) was 99.1 area %. The ratio of the 1,3-isomer and the 1,5-isomer was 30.4:69.6. In the synthesis of the pyrazole from DMAE, the total pyrazole yield was 92.7%; and the yield of the 1,3-somer was 28.2%.

Example 2

The same experiment as that of Comparative Example 2 was carried out, except that an aqueous solution of 8.6 g of potassium hydroxide (KOH, 1.4 equivalent relative to DFAAE) in 9.0 g of water was used in place of 9.0 g of water. In this experiment, 20.5 g of a crude pyrazole was yielded (crude product yield: 91.4%). The crude pyrazole was dissolved in acetone. The thus-obtained acetone solution was analyzed by a gas chromatograph. As a result, it was confirmed that the total pyrazole purity was 99.3 area %. The ratio of the 1,3-isomer and the 1,5-isomer was 98.5:1.5. In the synthesis of the pyrazole from DMAE, the total pyrazole yield was 90.7%; and the yield of the 1,3-somer was 89.4%.

Example 3

The same experiment as that of Comparative Example 2 was carried out, except that an aqueous solution of 6.2 g of sodium hydroxide (NaOH, 1.4 equivalent relative to DFAAE) in 9.0 g of water was used in place of 9.0 g of water. In this experiment, 21.5 g of a crude pyrazole was yielded (crude product yield: 95.8%). The crude pyrazole was dissolved in acetone. The thus-obtained acetone solution was analyzed by a gas chromatograph. As a result, it was confirmed that the total pyrazole purity was 72.6 area %. The ratio of the 1,3-isomer and the 1,5-isomer was 92.7:7.3. In the synthesis of the pyrazole from DMAE, the total pyrazole yield was 69.6%; and the yield of the 1,3-somer was 64.5%.

Example 4

The same experiment as that of Comparative Example 2 was carried out, except that a solution of Et$_3$N (11 g) in 9.0 g of water was used in place of 9.0 g of water. In this experiment, 20.6 g of a crude pyrazole was yielded (crude product yield: 91.8%). The crude pyrazole was dissolved in acetone. The thus-obtained acetone solution was analyzed by a gas chromatograph. As a result, it was confirmed that the total pyrazole purity was 96.3 area %. The ratio of the 1,3-isomer and the 1,5-isomer was 59.6:40.4. In the synthesis of the pyrazole from DMAE, the total pyrazole yield was 88.4%; and the yield of the 1,3-somer was 52.7%.

Reference Example 1

A solution of DFAAE in toluene was obtained in an amount of 384 g by washing 463 g of the reaction solution obtained in Synthesis Example 1, twice, with 250 g of water. When 10 g of this solution was subjected to solvent distillation, 2.45 g of DFAAE was obtained. Based on the theoretical yield of DFAAE in the reaction of Synthesis Example 1, the recovery rate of DFAAE by washing with water was 90%.

Then, the same experiment as that of Comparative Example 2 was carried out by using 113 g of the above-obtained DFAAE-toluene solution (DFAAE: 0.12 mol) without changing the amounts of the other substrates. In this experiment, 21.3 g of a crude pyrazole was yielded (crude product yield: 87.0%). The crude pyrazole was dissolved in acetone. The thus-obtained acetone solution was analyzed by a gas chromatograph. As a result, it was confirmed that the total pyrazole purity was 99.5 area %. The ratio of the 1,3-isomer and the 1,5-isomer was 92.5:7.5. In the synthesis of the pyrazole from DMAE, the total pyrazole yield was 86.6%; and the yield of the 1,3-somer was 80.1%.

The test results of Comparative Example 2, Examples 2 to 4 and Reference Example 1 are indicated in TABLE 2.

TABLE 2

| | Washing with water | Et3N•nHF salt | Base added | DFAAE (mol) | Crude pyrazole amount (g) |
|---|---|---|---|---|---|
| Comparative Example 2 | not done | present | none | 0.11 | 21.0 |
| Example 2 | not done | present | KOH | 0.11 | 20.5 |
| Example 3 | not done | present | NaOH | 0.11 | 21.5 |
| Example 4 | not done | present | Et$_3$N | 0.11 | 20.6 |
| Reference Example 1 | done | not present | none | 0.12 | 21.3 |

| | Pyrazole rate (area %) | Isomer ratio 1,3-isomer | Isomer ratio 1,5-isomer | Total pyrazole yield (%) | Yield (%) of 1,3-isomer |
|---|---|---|---|---|---|
| Comparative Example 2 | 99.1 | 30.4 | 69.6 | 92.7 | 28.2 |
| Example 2 | 99.3 | 98.5 | 1.5 | 90.7 | 89.4 |
| Example 3 | 72.6 | 92.7 | 7.3 | 69.6 | 64.5 |
| Example 4 | 96.3 | 59.6 | 40.4 | 88.4 | 52.7 |
| Reference Example 1 | 99.5 | 92.5 | 7.5 | 86.6 | 80.1 |

1,3-isomer: ethyl 3-(difluoromethyl)-1-methyl-1H-pyrazole-4-carboxylate
1,5-isomer: ethyl 5-(difluoromethyl)-1-methyl-1H-pyrazole-4-carboxylate
DFAAE: ethyl 2-(difluoroacetyl)-3-dimethylamino)acrylate
Total pyrazole yield: total yield of 1,3-isomer and 1,5-isomer
Total pyrazole yield (%) = {crude pyrazole amount (g) × pyrazole rate (area %)}/{DFAAE (mol) × 204 (molecular weight)}
Yield (%) of 1,3-isomer = total pyrazole yield (%) × (isomer ratio of 1,3-isomer)

As is seen from TABLE 2, the 1,3-disubstituted pyrazole-4-carboxylic acid ester was produced more efficiently by the use of the inorganic base than by the use of the organic base in the cyclization reaction. When the cyclization reaction was performed by the addition of the inorganic base without removing the salt from the reactor content obtained by the acylation reaction, the 1,3-disubstituted pyrazole-4-carboxylic acid ester was efficiently obtained by limiting the amount of generation of the 1,5-isomer.

Synthesis Example 2

A 1000-ml three-neck flask was equipped with a blowing tube, a thermometer and a dry-ice condenser and sealed with nitrogen. Into this flask, 72 g of ethyl 3-N,N-dimethylaminoacrylate (DMAE), 285 g of toluene and 56 g of triethylamine (Et$_3$N) were placed. The resulting solution was stirred while cooling the flask in a water bath. Then, 56 g of difluoroacetic acid fluoride (purity: 95%) was introduced at a rate of 0.5 g/min into the flask reactor through the blowing tube After completion of the introduction, the reaction was continued for 1 hour by stirring the reaction solution at 30° C. and completed.

The amount of the reactor content (reaction solution) thus obtained was 463 g. The reaction solution was washed twice with 250 g of water to remove therefrom Et$_3$N.nHF salt. With this, 382 g of 25.9 mass % DFAAE-toluene solution was obtained.

A 2000-ml three-neck flask was equipped with a dropping funnel and a thermometer and sealed under a nitrogen balloon. Into this flask, 36.0 g of water, 6.4 g of sodium hydroxide, 400 ml of toluene and 24.0 g (0.52 mol) of monomethylhydrazine were placed. The resulting solution was cooled, with stirring, to −10° C. or lower in a low-temperature thermostat whose temperature was set to −15° C. Then, 375 g of the water-washed DFAAE-toluene solution (DFAAE: 0.11 mol) was gradually dropped into the flask through the dropping funnel in such a manner that the inside temperature of the flask did not exceed −10° C. After completion of the dropping, the solution was kept stirred for 1 hour at −12° C. The inside temperature of the flask was then raised to 0° C. The thus-obtained solution was separated with the addition of 400 ml of water. The organic phase was recovered by a separatory funnel and washed with 400 ml of water, thereby yielding 702 g of 9.7 mass % pyrazole-toluene solution.

Hydrochloric Acid Washing Examples 1 to 4

Into a three-neck flask with a thermometer and a reflux condenser, 150 g of the pyrazole-toluene solution obtained in Synthesis Example 2 and 50 g of hydrochloric acid having a concentration shown in TABLE 3 (35 mass %, 25 mass %, 17 mass %, 10 mass %) were placed. The resulting mixture was stirred at room temperature (25° C.) for 1 hour. Then, the separated organic phase was concentrated. The thus-obtained crude pyrazole was analyzed by high precision liquid chromatography (HPLC) according to the following analysis method and sample preparation method.

<HPLC Analysis Method>
Analytical equipment: Agilent HP-1000 LC system
Flow rate: 1 ml/min
6 mM methanesulfonic acid: ACN=6:4, gradually changed to 3:7 over 30 minutes
UV detector: λ=210 nm
Column: Cadenza CD-C18 (diameter: 4.6 mm, length: 250 mm, particle size: 3 μm)
Temperature: 35° C.

<Sample Preparation Method>

A sample was taken and purged with nitrogen to remove therefrom the solvent. After that, the weight of the sample was measured. A mobile phase was then added to the sample to a concentration of 2 mg/ml (6 mM methanesulfonic acid: ACN=6:4), followed by dissolving the sample uniformly in the mobile phase. The resulting sample solution was subjected to analysis.

The test results of Hydrochloric Acid Washing Examples 1 to 4 are indicated in TABLE 3.

TABLE 3

| Hydrochloric Acid | Recovery rate (%) | Retention time (min)/Composition (area %) | | | | | |
|---|---|---|---|---|---|---|---|
| | | 2.25 | 2.45 | 3.51 | 3.74 | 4.4 | 5.63 |
| Before purification | — | 0.016 | 0.035 | 0.071 | 0.000 | 0.041 | 0.019 |
| 35% | 64 | 0.000 | 0.030 | 0.000 | 0.026 | 0.000 | 0.000 |
| 25% | 96 | 0.000 | 0.031 | 0.000 | 0.085 | 0.000 | 0.000 |
| 17% | >99 | 0.000 | 0.030 | 0.000 | 0.012 | 0.000 | 0.000 |
| 10% | >99 | 0.000 | 0.031 | 0.015 | 0.000 | 0.000 | 0.000 |

| Hydrochloric Acid | Retention time (min)/Composition (area %) | | | | | | | |
|---|---|---|---|---|---|---|---|---|
| | 5.76 | 5.87 | 6.1 | 7.1 | 7.37 | 8.52 | 11.81 | 12.32 |
| Before purification | 0.044 | 0.022 | 0.040 | 0.017 | 0.038 | 97.396 | 0.045 | 0.217 |
| 35% | 0.000 | 0.013 | 0.000 | 0.000 | 0.000 | 92.491 | 0.000 | 0.573 |
| 25% | 0.000 | 0.000 | 0.000 | 0.000 | 0.000 | 97.093 | 0.012 | 0.202 |
| 17% | 0.000 | 0.000 | 0.000 | 0.000 | 0.000 | 98.990 | 0.019 | 0.071 |
| 10% | 0.000 | 0.000 | 0.020 | 0.000 | 0.018 | 97.507 | 0.013 | 0.218 |

3.51: ethyl 3-N,N-dimethylaminoacrylate
3.74: 3-(difluoromethyl)-1-methyl-1H-pyrazole-4-carboxylic acid
7.37: ethyl 2-(difluoroacetyl)-3-(dimethylamino)acrylate
8.52: ethyl 3-(difluoromethyl)-1-methyl-1H-pyrazole-4-carboxylate
12.32: ethyl 5-(difluoromethyl)-1-methyl-1H-pyrazole-4-carboxylate As is seen from TABLE 3, the 1,3-disubstituted pyrazole-4-carboxylic acid ester was purified efficiently by washing/contact of the reaction solution with hydrochloric acid.

As described above, it is possible in the present invention to produce the 1,3-disubstituted pyrazole-4-carboxylic acid ester at a high yield and selectivity and with less discoloration. It is also possible to limit the amount of an isomer (1,5-disubstituted pyrazole-4-carboxylic acid ester) in the product to a low level in the present invention.

INDUSTRIAL APPLICABILITY

The method according to the present invention is useful for production of a pyrazole compound that is useful as an intermediate for pharmaceutical and agrichemical products.

The invention claimed is:

1. A method for producing a pyrazole compound of the general formula (5), comprising:
a first reaction step of obtaining a reactor content containing a 2-acyl-3-aminoacrylic acid ester of the general formula (1) by reaction of difluoroacetic acid fluoride with a dialkylaminoacrylic acid ester of the general formula (3) in the presence of an organic base; and
a second reaction step of forming the pyrazole compound of the general formula (5) by mixing the reactor content obtained by the first reaction step with a substituted hydrazine of the general formula (4) and an inorganic base

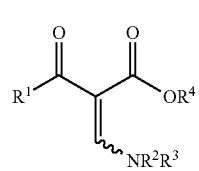

where $R^1$, $R^2$, $R^3$ and $R^4$ each independently represent an alkyl group

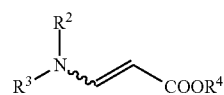

where $R^2$, $R^3$ and $R^4$ have the same meanings as in the general formula (1)

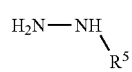

wherein $R^5$ represents an alkyl group or an aryl group

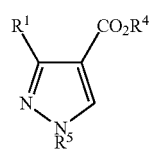

wherein $R^1$, $R^4$ and $R^5$ have the same meanings as above.

2. The method for producing the pyrazole compound according to claim 1, wherein the inorganic base is an alkali metal hydroxide.

3. The method for producing the pyrazole compound according to claim 1, wherein $R^1$ is a halogenated alkyl group of 1 to 10 carbon atoms.

4. The method for producing the pyrazole compound according to claim 3, wherein $R^1$ is a fluoroalkyl group of 1 to 4 carbon atoms.

5. The method for producing the pyrazole compound according to claim 4, wherein $R^1$ is a trifluoromethyl group or a difluoromethyl group.

6. The method for producing the pyrazole compound according to claim 3, wherein $R^1$ is a chloroalkyl group of 1 to 4 carbon atoms.

7. The method for producing the pyrazole compound according to claim 6, wherein $R^1$ is a dichloromethyl group.

8. The method for producing the pyrazole compound according to claim 1, wherein, in the second step, the pyrazole compound of the general formula (5) is formed by mixing a composition containing the reactor content obtained by the first step and the inorganic base with a composition containing the substituted hydrazine.

9. The method for producing the pyrazole compound according to claim 1, wherein the organic base used in the first step is a tertiary amine; and wherein the inorganic base used in the second step is either potassium hydroxide or sodium hydroxide.

* * * * *